United States Patent
Mauger et al.

(10) Patent No.: US 9,338,567 B2
(45) Date of Patent: May 10, 2016

(54) AUDITORY SIGNAL PROCESSING

(71) Applicant: Cochlear Limited, Macquarie University (AU)

(72) Inventors: Stefan Mauger, Macleod (AU); Mohit Shivdasani, Heidlberg Heights (AU)

(73) Assignee: Cochlear Limited, Sydney (AU)

( * ) Notice: Subject to any disclaimer, the term of this patent is extended or adjusted under 35 U.S.C. 154(b) by 0 days.

(21) Appl. No.: 14/408,214

(22) PCT Filed: Jun. 14, 2013

(86) PCT No.: PCT/IB2013/054865
§ 371 (c)(1),
(2) Date: Dec. 15, 2014

(87) PCT Pub. No.: WO2013/186743
PCT Pub. Date: Dec. 19, 2013

(65) Prior Publication Data
US 2015/0117690 A1    Apr. 30, 2015

(30) Foreign Application Priority Data
Jun. 14, 2012    (AU) ............................... 2012902484

(51) Int. Cl.
*H04R 25/00* (2006.01)
*A61N 1/36* (2006.01)
*A61N 1/05* (2006.01)

(52) U.S. Cl.
CPC ............... *H04R 25/606* (2013.01); *A61N 1/36* (2013.01); *A61N 1/36032* (2013.01); *A61N 1/0541* (2013.01)

(58) Field of Classification Search
CPC ............... H04R 25/00; H04R 2225/49; H04R 2460/01; H04R 2460/13
USPC .................. 381/312, 316–317, 320–321, 326; 600/25
See application file for complete search history.

(56) References Cited

U.S. PATENT DOCUMENTS

| | | | |
|---|---|---|---|
| 6,236,731 B1 * | 5/2001 | Brennan et al. | 381/316 |
| 2009/0118795 A1 * | 5/2009 | Ibrahim et al. | 607/57 |
| 2010/0290651 A1 * | 11/2010 | Grayden et al. | 381/312 |

* cited by examiner

*Primary Examiner* — Suhan Ni
(74) *Attorney, Agent, or Firm* — McDonnell Boehnen Hulbert & Berghoff LLP

(57) ABSTRACT

Methods, systems, and devices for processing an auditory signal to generate auditory prosthesis electrode stimuli in response to an incoming acoustic signal are disclosed. An example method includes dividing the incoming acoustic signal into one or more frequency envelopes. The example method also includes determining which auditory prosthesis electrodes to stimulate. The example method additionally includes determining a temporal reference point to which auditory prosthesis electrode stimuli are referenced. The example method further includes determining a delay for each of the auditory prosthesis electrode stimuli from the temporal reference point. The example method yet further includes determining amplitudes of the auditory prosthesis electrode stimuli. The example method also includes determining a wait period length before each successive temporal reference point.

15 Claims, 3 Drawing Sheets

AUDITORY SIGNAL PROCESSING

CROSS-REFERENCE TO RELATED APPLICATION

Priority is claimed to Australian Provisional Patent Application No. 2012902484 filed on Jun. 14, 2012, and to International Patent Application No. PCT/IB2013/054865 filed on Jun. 14, 2013, the contents of each of which are hereby incorporated by reference.

FIELD OF THE INVENTION

The field of the invention involves auditory signal processing methods, auditory prosthesis, and systems for providing electrical stimulus via an auditory prosthesis to a patient having a hearing deficiency.

BACKGROUND

In normal hearing, sound signals are converted into electrical impulses that are perceived by the brain as sound. Conditions which affect the auditory system can result in a range of hearing impairments. The perception of auditory signals that are received by a hearing impaired patient may be improved by prosthetic implants that incorporate a microphone, a signal processor and an electrode array for delivering representative electrical signals to the patient. The signal processor converts auditory signals into electrical signals in order to convey the sound to the patient. Of particular importance to patients having a hearing deficiency is in regard to the comprehension of speech.

Some conditions can be overcome by hearing aids and result in near normal hearing and good speech understanding. However, some conditions which lead to more severe hearing loss cannot be overcome with conventional hearing aids. These pathologies can be overcome by implanting auditory neural prostheses which bypass the damaged part of the auditory system and typically activate the auditory system through electrical stimulation to provide the perception of sound. Cochlear implants, auditory brainstem implants and auditory midbrain implants are all examples of such auditory neural prostheses.

Auditory signals (sounds) may be described as having various elements such as loudness (amplitude) and pitch as well as varying over time. Each of these parameters must be considered when developing an auditory signal processing method. A signal processing method is a predetermined instruction set for producing electrode stimulus instructions from received sound signals.

The nature of the normal function of hearing has previously been described (U.S. Pat. No. 5,271,397). In particular, when normal speech is analysed it is found that several frequency peaks are produced simultaneously. This provides the nature of the sound and the characteristics of speech interpretation. The frequency peaks, known as formants, are numbered from the glottal pulse, F0, with higher frequency peaks being the first formant, F1, second formant, F2 and so on. Different vowel sounds change the frequency and amplitude of these formants, and in particular, the second formant F2.

In an auditory prosthesis, there are two basic methods by which neural information may be coded, the rate code and the temporal code. The rate code uses the number of neural firing events over a short time period to code auditory features. The temporal code uses the temporal position of firing events of each neuron to code auditory features. In an auditory prosthesis, the rate code is transmitted using the power of the incoming stimuli; low power electrical stimuli produce lower electrical stimulation rates, higher power electrical stimuli produce higher rates. On the other hand, the temporal code could be achieved in an auditory prosthesis by the precise presentation of electrical stimuli in time.

In regards to the pitch aspect of the signal processing strategy, the frequency is measured in Hertz (Hz), which may vary from low sounds to high sounds in a range from 20 Hz to 20,000 Hz. The auditory signal processing method divides the auditory signal into bands of frequencies, one method being to divide the signal into frequency bands approximating a quarter of an octave (PCT/AU00/00838).

Alternatively, a spatio-temporal pattern of stimulation along the length of an intra-cochlea electrode array may be produced which delays more apical stimuli (PCT/AU01/00723). This mimics the spatio-temporal pattern associated with the travelling wave observed on the basilar membrane in anacoustically excited normally-hearing cochlea. Although this strategy mimics a known physiological process adding a fixed delay to each electrode to compensate for bypassed processes, it essentially carries no additional information regarding the incoming signal. It merely changes the time that the information is provided through the electrode.

Simultaneous stimulation of the electrodes is not conducive to eliciting a perception of sound that is faithful to the actual incoming acoustic signal. This is because if electrodes are stimulated simultaneously, current paths between electrodes can interact, causing undesirable stimulation. Therefore, most existing cochlear strategies have been developed to stimulate only one electrode at a time.

The aspect of a signal processing strategy that relates to the variation of an auditory signal over time is known as temporal variation. It has previously been known to divide an incoming auditory signal into discrete time periods known as "timeslices" in order that the corresponding electrical signal from each timeslice may be delivered by a stimulation pulse to an appropriate electrode within the auditory prosthesis. Each timeslice incorporates the total time taken to receive, process, deliver and recover from the stimulus.

Various auditory signal processing methods have previously been described, such as CIS (U.S. Pat. No. 4,207,441) and SPEAK (U.S. Pat. No. 5,597,380). In these methods, the duration of each timeslice is fixed to a predetermined rate. In another strategy, described in PCT/AU00/00838, the stimulation rate is not fixed, but determined according to attributes contained within the incoming auditory signal.

Alternatively, the time of stimulus of each electrode may be synchronised to the temporal peak in the filter output of the sound signal. The time of stimulation being set to stimulate at the time that positive peaks occur in each frequency band (AU 2002312636).

A temporal adjustment may also be made to the electrode activation time such that the activation of lower amplitude components of the signal is delayed relative to activation of higher amplitude components of the incoming sound signal (PCT/AU2004/001729).

These auditory signal processing methods such as PCT/AU03/00639 (STAR) include generating a series of electrical stimulation "spikes" from each sound signal, where each spike has a temporal position based on the time at which the sound signal crossed a pre-determined threshold in a positive direction. The value of the threshold is adjustable in order to take account of differing listening conditions and levels of background noise. Explicit extraction of pitch is not required to control the rate of stimulation. This strategy adds additional information to the signal through the varied rate of stimulation that is used on each electrode, since stimulus rate does affect frequency precepts. Although some temporal information is added to the signal through this process, it is expected to be limited since stimuli are independently derived from the band pass signal in each electrode channel and not relative to each other.

Other auditory signal processing methods have been developed with a view to modifying the electrical stimulation of the electrodes to reflect the natural delay which occurs between an auditory signal reaching one ear and the other (interaural time delay). For instance, PCT/AU02/00660 describes the synchronization of the timing of the electrode stimuli with the temporal peak in the amplitude of the corresponding incoming band-pass filtered auditory signal. This provides advantages to patients having an auditory prosthesis in each ear, conveying the time-of-arrival differences between the ears.

Despite the progress made by existing auditory prostheses, signal processors and signal processing strategies, the perception of sound by hearing impaired patients remains imperfect and problematic. None of the temporal strategies described above have a global time point to which electrical stimuli are referenced. Furthermore, these strategies may involve generation of continuous stimulation, not allowing a particular sequence of pulses to be processed by the brain before the next sequence of pulses is delivered. It is therefore desirable to provide improved signal processing methods, auditory prostheses and systems.

SUMMARY OF THE INVENTION

Accordingly the current invention provides an auditory signal processing method for generating auditory prosthesis electrode stimuli by an auditory prosthesis in response to an incoming acoustic signal, the auditory signal processing method including the following steps:

dividing the incoming acoustic signal into frequency envelopes;

determining which auditory prosthesis electrodes are to be stimulated;

determining a temporal reference point (gated reset) to which auditory prosthesis electrode stimuli are referenced;

determining a delay for each auditory prosthesis electrode stimuli from the 15 temporal reference point;

determining amplitudes of auditory prosthesis electrodes stimuli; and determining a wait period length before each successive temporal reference point.

As described herein, the auditory signal processing method may conveniently be referred to as the TIGER [Temporally Invoked Gated Electrical Reset] auditory signal processing.

Preferably, the temporal reference point is a gated reset that denotes the start of a stimulation window. The auditory signal processing method does not have a fixed stimulation rate, but instead has a "gated reset," which denotes the start of a stimulation window. All stimuli in the stimulus window are then referenced to the gated reset. The advantage of a gated reset is that temporal information can be referenced to a time point.

A gated reset may be invoked by content of the incoming auditory signal. For example, the incoming auditory signal may include features of speech such as the glottal pulse, formants, positive zero crossings, vowels, plosive and implosive bursts, voiced or unvoiced consonants, nasal consonants, trills, taps, flaps, fricatives, approximants, clicks, and ejectives associated with consonants, whether produced by any of the following means: bilabial, labiodental, dental, alveolar, post alveolar, retroflex, palatal, velar, uvular, pharyngeal, or glottal.

The temporal neural code uses the timing of neural impulses to code information and therefore stimulates different electrodes at various time points and delays, but these delays need to be temporally related to something. It has been suggested that these "delays" may be relative to other neural impulses, groups of impulses, or even to large scale neural structure oscillations. A feature of the current invention is to deliver an electrical stimuli sequence which can provide the auditory system with relative temporal differences which can be used by the brain's temporal coding mechanism. This additional temporal information enhances the pitch information of acoustic stimuli which are important in speech and music perception. Pitch information is not currently well represented by current stimulation strategies relying primarily on activating the neural rate-place code.

Still more preferably, the temporal reference point determines the start of an electrode stimulation window, to which all events in the stimulation window are referenced.

The auditory signal processing method as hereinbefore defined may delay stimulation of the auditory prosthesis electrode stimuli corresponding to one or 25 more of the frequency envelopes when compared with one or more of the other frequency envelopes. Optionally, the magnitude of the delay is a function of the amplitude of the frequency envelope and/or a function of the frequency of the frequency envelope.

The auditory signal processing method may further include the step of providing a wait period of no electrical stimulation after a stimulation window, prior to any subsequent electrode stimulation window. This allows for the electrical stimuli from a stimulus window to be processed together before further stimuli are delivered reducing or preventing overlapping stimulation.

The auditory signal processing method may provide electrical stimulation to a single electrode during a single stimulus period using single pulses, a periodic pulse train, a group of non periodic pulses, no pulses or asynchronous pulses. Across electrodes during a single stimulus period, stimuli may be either interleaved or concurrent electrical pulses. The auditory signal processing method may also have forms of grounding such as common ground, multipolar, bipolar or monopolar.

In another aspect, there is provided a system of stimulating an auditory prosthesis electrode array including a microphone, a signal processor, and an electrode array, wherein the signal processor uses a signal processing method for generating auditory prosthesis electrode stimuli by an auditory prosthesis in response to an incoming acoustic signal, the auditory signal processing method including the following steps:

dividing the incoming acoustic signal into frequency envelopes;

determining which auditory prosthesis electrodes are to be stimulated, determining a temporal reference point to which auditory prosthesis electrode stimuli are referenced, determining a delay for each auditory prosthesis electrode stimuli from the temporal reference point, determining amplitudes of auditory prosthesis electrode stimuli; and determining a wait period length before each successive temporal reference point.

In yet another aspect, there is also provided an auditory prosthesis having a signal processor for converting an acoustic signal into an electrical signal, wherein the signal processor uses a signal processing method for generating auditory prosthesis electrode stimuli by an auditory prosthesis in response to an incoming acoustic signal, the auditory signal processing method including the following steps:

dividing the incoming acoustic signal into frequency envelopes;

determining which auditory prosthesis electrodes are to be stimulated;

determining a temporal reference point to which auditory prosthesis electrode stimuli are referenced;

determining a delay for each auditory prosthesis electrode stimuli from the temporal reference point;

determining amplitudes of auditory prosthesis electrode stimuli; and determining a wait period length before each successive temporal reference point The auditory prosthesis may be used to assist or bypass damaged parts of the auditory system, for example such prostheses include cochlear implants, auditory brainstem implants and auditory midbrain implants.

DETAILED DESCRIPTION

Any discussion of documents, devices, acts or knowledge in this specification is included to explain the context of the invention. It should not be taken as an admission that any of the material formed part of the prior art base or the common general knowledge in the relevant art on or before the priority date of the claims herein.

Figure 1:
FIG. 1 shows a diagrammatic representation of a cochlear implant signal path.

FIG. 1 shows a diagrammatic representation of a cochlear implant signal path. The acoustic signal from a microphone or other device is received by the cochlear implant. If the input signal is too loud then the Automatic Gain Compression (AGC) will attenuate the input signal to a comfortable level. The signal is then separated into frequency bands through the Fast Fourier Transform (FFT), and combined into frequency channels, providing an envelope of the auditory signal representing each electrode. The adaptive dynamic range optimisation (ADRO) then applies a further gain to the signal to present it in the middle of preferred loudness range. The signal envelope is then used to create electrical pulse trains, which are presented to the electrode.

Figure 2:
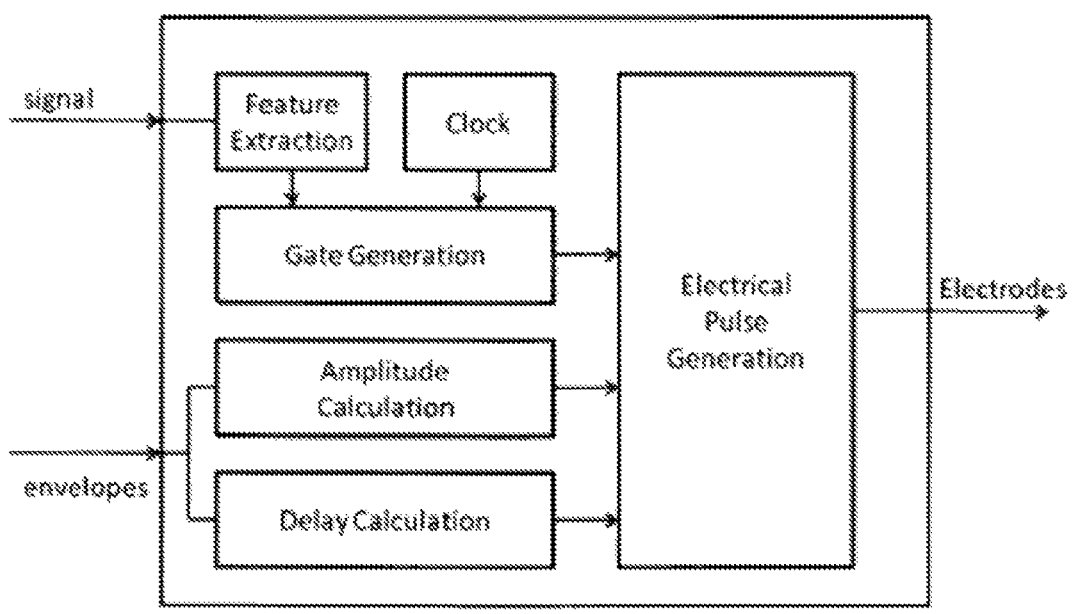
FIG. 2 shows a diagrammatic representation of the auditory signal processing method.

FIG. 2 shows a diagrammatic representation of the auditory signal processing method. The incoming auditory signal is processed to extract the desired feature, or a clock generates time points that are used by the gated reset generation block to initiate a start of a gated reset. The gated reset generation block may also generate information about the required wait period. The signal envelopes are processed by an amplitude calculation block, which takes the envelope amplitude and converts this to an electrical pulse power. The signal envelopes are also used to calculate the desired delay from the gated reset. The electrical pulse generator combines the gated reset, the delay from the gated reset and the amplitude of the signal to create the desired pulse train. This pulse train is presented to the electrodes.

Figure 3:
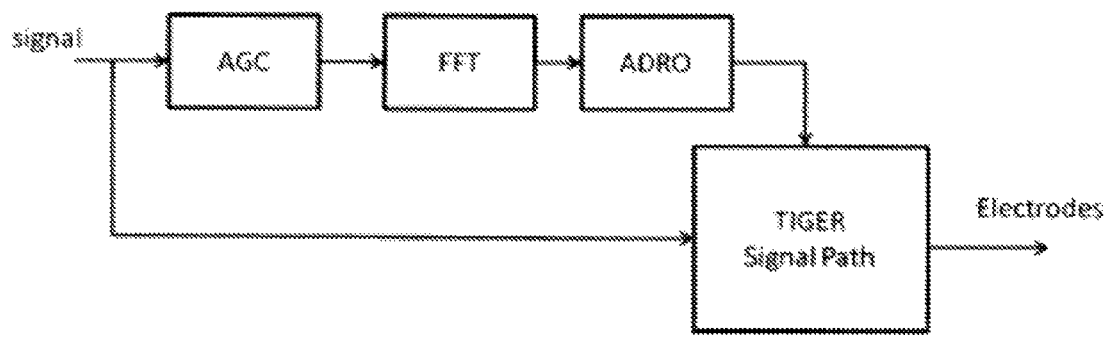
FIG. 3 is a diagrammatic representation of the auditory signal processing method signal path presented in the cochlear implant signal path.

FIG. 3 shows a diagrammatic representation of the auditory signal processing method signal path presented in the cochlear implant signal path. The auditory signal processing method signal path receives both the signal envelopes as well as the original signal. The auditory signal processing method incorporates temporal information through electrical auditory stimulation in an auditory prosthesis in order to convey additional information of the auditory environment and aid in pitch, music and speech perception. The auditory signal processing method may include identifying a reference time point from which to present subsequent electrical stimuli. This reference time point may either be generated from an internal process or from a feature of the incoming acoustic input signal. The auditory signal processing method may also include the calculation of delays for each of the electrical stimuli that are to be delivered to individual electrodes relative to this time point. The delays can be derived either from a feature of the acoustic signal or from the band limited signal representing each electrode. Upon presentation of a single sequence of stimuli to all the relevant electrodes, the auditory signal processing method allows for a period of no stimulation (wait time) of a fixed length, or of a variable length until the next reference time point is derived.

The auditory signal processing method was developed to incorporate temporal information found in speech and to provide a "base" stimulation strategy, and may be used to stimulate anywhere in the auditory system, i.e.: cochlear implants, auditory nerve implants, brainstem implants, midbrain implants, or cortical implants.

One method of determining the gated reset is to use the fundamental frequency of the signal as the feature frequency. Many methods are available to determine the fundamental frequency of a signal (Hess W, PITCH DETERMINATION OF SPEECH SIGNALS, Berlin: Springer-Verlag, 1983). Once the fundamental frequency of the signal is obtained, the period F. can be calculated by taking the reciprocal of the fundamental frequency F0. At the end of a wait period, a new feature period $F_n$ is calculated and used to determine the length of the next stimulus window, which is broken into two sections: stimulus period $\alpha(1)$ and wait period $\phi(1)$. In the case where a feature frequency is unable to be calculated, a predetermined period can be used to create gated resets for electrical stimulation to be referenced against.

The auditory signal processing method initially divides an incoming acoustic 20 signal into its frequency components. This is common to many previous stimulation strategies which achieve this task through filter bank, although to convey additional temporal information, methods such as wavelets or Gabor filters may also be appropriate (Olshausen 2002). The aim of the filter banks would be to separate frequency components, while retaining as much fine temporal information as possible. Frequency components are then processed further to find their frequency envelopes.

The auditory signal processing method further includes the temporal spacing of stimuli. A gated reset can be invoked by content of the acoustic signal such as F0 (or F1, F2) or other content within the acoustic signal, an external trigger, or a combination of both or inherently within the implant system. For instance, while voiced speech segments are present, a gated reset could be invoked at a certain phase of the glottal pulse. When no strong F0 feature is found during an unvoiced speech segment, a fixed gated reset rate of 350 Hz may be used. This reset signal determines the start of a stimulation window to which all events in the stimulation window are referenced. All previous stimulation strategies have no temporal reference. Electrical stimuli delays for each frequency channel delivered to all relevant individual electrodes are determined from information from the input signal and referenced to the gated reset.

Delays relative to the gated reset can be calculated for each electrode by the equation:

$$\Delta t(l) = \alpha(l)\left(1 - \frac{A(l) - A_{min}}{A_{max} - A_{min}}\right) \qquad (1)$$

Where $\Delta t(l)$ is the delay to be applied to electrical stimuli relative to a gated reset in each analysis window, $\alpha(l)$ is the maximum delay of stimuli within an analysis window for any electrode, $A(l)$ is the power amplitude of the signal envelope, and $A_{max}$ is the maximum permissible signal envelope.

An example of this stimulation strategy using the fundamental frequency of a signal as the feature to be extracted to initiate the gated reset. In this example a single pulse with a delay as determined will be described.

In general, the fundamental frequency of a male's voice ranges from 85 Hz to 150 Hz. The fundamental frequency of a female's voice ranges from 165 Hz to 255 Hz, giving a total range of fundamental frequencies for adults of 85 Hz to 255 Hz. The following example shows delay calculations of this simple implementation of this strategy. A maximum feature frequency (slightly higher than the expected 255) of 286 is used to determine parameter values for this example. The maximum feature frequency would have a minimum period of $1/286 = F_n = 3.5$ ms. Allowing a minimum weight period of 0.5 ms, a maximum stimulus delay ($\alpha(l)$) of 3 ms is used. If a fundamental frequency higher than this is encountered, then it should be accepted to alias. Also, if the minimum feature frequency is less than 85 Hz, a pre-determined feature frequency should be used. For this example using a maximum stimulus delay of 3 ms and using A as the signal strength in dB, delays for three channels with intensities of 75, 60, and 35 dB are calculated by the delay equation (1), which results in delays from the gated reset for these three channels of:

$$\Delta t(l) = 3\left(1 - \frac{75 - 25}{75 - 25}\right) = 0 \text{ ms} \qquad (2)$$

$$\Delta t(l) = 3\left(1 - \frac{60 - 25}{75 - 25}\right) = 0.9 \text{ ms} \qquad (3)$$

$$\Delta t(l) = 3\left(1 - \frac{35 - 25}{75 - 25}\right) = 2.4 \text{ ms} \qquad (4)$$

Figure 5:
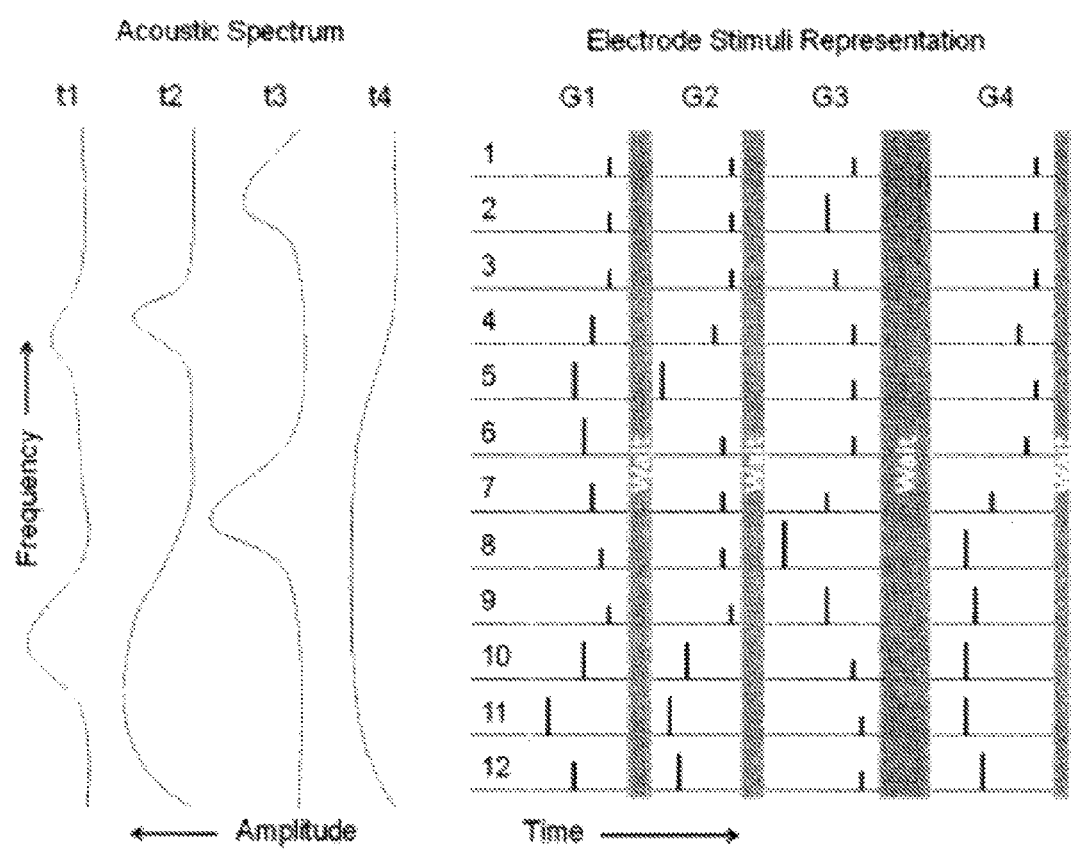
FIG. 5 shows a diagrammatical representation of the spectral amplitude of a signal.

The delay $\Delta t(l)$ can have a range from zero to $\alpha(l)$. FIG. 5, for example, shows a diagrammatical representation of the spectral amplitude of a signal at four time points (t1, t2, t3, t4), and a possible electrical signal output on 12 electrodes for the four time points (G1, G2, G3, G4).

When stimulation for a given window have finished, the auditory signal processing method may enter a wait period where there are no stimuli until another gated reset is invoked. A wait period provides a period of no stimulation between the end of a stimulation window and the next gated reset. This allows for the stimuli from a given stimulus window to be perceived together before more stimuli are delivered. The present invention not only has periods of no stimulation but these wait periods can be time varying. The wait period provides the start of the next window to be distinct from the previous window.

Wait periods may be calculated by the equation $$\phi(l) = F_n - \alpha(l) \qquad (5)$$

Where $\phi(l)$ is the wait period of no stimulation before the subsequent gated reset is initiated, $F_n$ is a feature period in milliseconds determined from the input signal (in the best example, the fundamental formant F0 period and a pre-determined period when F0 cannot be reliably estimated), and $\alpha(l)$ is the maximum required delay in milliseconds within an analysis window across all electrodes.

The requirement to have a wait period is: $\alpha(l) < F_n$.

Demonstrating that the maximum delay of stimuli across electrodes $\alpha(l)$ must be shorter than the feature period $F_n$.

Example

For a minimum feature period of 3.5 ms or a longer feature length of 8 ms, equation (5) can be used to calculate the wait period for these stimulus frames:

$$\phi(l) = 3.5 - 3 = 0.5 \text{ ms} \qquad (6)$$

$$\phi(l) = 8 - 3 = 5 \text{ ms} \qquad (7)$$

In a stimulus window many types of stimuli can be used including: single pulses, periodic pulse train, or a group of non periodic pulses, or no pulses, but all stimuli must be temporally referenced to the gated reset. For high rate stimulation, a single pulse may be represented by a group of very closely spaced pulses. That is, a single pulse referenced to the gated reset may be described by a set of pulses, with the first pulse in the set of pulses referenced to the gated reset.

Different types of grounding may be needed for desired stimulus pulses. The auditory signal processing method allows for the selection of monopolar, bipolar, multipolar, or common ground stimulation for a stimulation pulse. One such use for various grounding methods within a stimulus window or between stimulus windows would be to influence the spread of current. For example when a speech signal is broad banded, monopolar stimulation may be used and where a speech signal is narrow banded bipolar stimulation may be used.

If interleaved stimulation is needed for a specific application, and if multiple stimuli are given the same delay, then an additional process to temporally un-align stimuli with the minimum temporal shift allowed by the maximum stimulation rate of the neural implant could be used. Alternatively, only one of the stimulus pulses could be stimulated in one window, and the other in the subsequent window. If simultaneous stimulation is possible, then the appropriate amplitude signals should be presented, taking into account the summation of electrical stimulation.

Figure 4:
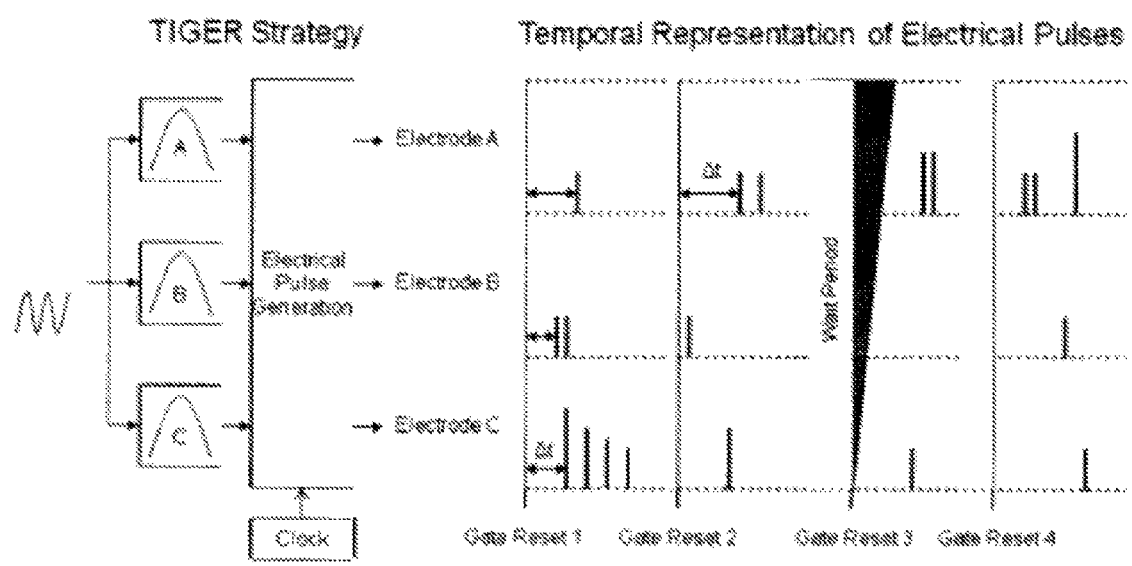
FIG. 4 shows a diagrammatic representation of a system with three frequency bands and three electrodes.

A travelling wave addition may also be used where the gated reset incorporates the known delay of wave propagation in the cochlea. In one embodiment of the invention this may be represented by delays due to signal amplitude being referenced to a frequency specific delay demonstrated in FIG. 4, which shows a diagrammatic representation of a system with three frequency bands and three electrodes. The incoming auditory signal is filtered by band pass filters. The auditory signal processing method presents electrical pulses to each electrode. Electrical pulses are referenced from the gated resets through temporal delays $\Delta t$. A set of pulses may delayed with reference to the gated reset. A travelling wave may be added to the gated reset to delay pulses further depending on the channel frequency. The wait period may be of varying length. A stimulus pulse is not needed for each channel in each gated reset. One implementation of this could be to add a fixed delay as a function of frequency to compensate for the real delay found in the cochlea. Another implementation would be to have each channel with a fixed, but random delay between 0 and 8 ms, such as 0, 1, 2, 3, 4, 5, 6, 7 or 8 ms.

Within the context of the present invention, the term "wait" should be understood to refer to a period of time between auditory stimulation windows, whereas the term "delay" refers to the temporal relationship of features within a stimulation window.

The description of the present invention described with reference to the figures, is for the purpose of illustration only and is not intended to limit the generality of the subject invention as described. Various modifications may be made in details of design and construction (and process steps, parameters of operation, etc.) without departing from the scope of the invention. Those skilled in the art will appreciate that the invention described herein is susceptible to variations and modifications other than those specifically described. It is to be understood that the invention includes all such variations and modifications. The invention also includes all of the steps, features, and methods referred to or indicated in this specification, individually or collectively and any and all combinations of any two or more of said steps or features and methods.

"Comprises" or "comprising" and grammatical variations thereof when used in this specification are to be taken to specify the presence of stated features, integers, steps or components or groups thereof, but do not preclude the presence or addition of one or more other features, integers, steps, components or groups thereof.

The invention claimed is:

1. An auditory signal processing method, the method comprising:
   dividing an acoustic signal into one or more frequency envelopes;
   determining which electrodes of an auditory prosthesis to stimulate;
   determining a temporal reference point for stimulating the determined electrodes;
   determining, for each of the determined electrodes, a respective delay from the determined temporal reference point, wherein the respective delay defines how long to wait after the determined temporal reference point before stimulating the respective electrode;
   determining, for each of the determined electrodes, a respective amplitude based on an amplitude of one of the one or more frequency envelopes; and
   stimulating the determined electrodes of the auditory prosthesis by applying stimulus to each electrode with the electrode's determined delay and amplitude.

2. The method according to claim 1, wherein the temporal reference point is a gated reset.

3. The method according to claim 2, wherein the gated reset is invoked by content of the acoustic signal.

4. The method according to claim 3, wherein the temporal reference point determines the start of an electrode stimulation window, and to which all events in the stimulation window are referenced.

5. The method according to claim 3, wherein determining, for each of the determined electrodes, a respective delay from the determined temporal reference point comprises determining the respective delay based on a frequency of a respective one of the one or more frequency envelopes.

6. The method according to claim 3, wherein determining, for each of the determined electrodes, a respective delay from the determined temporal reference point comprises determining the respective delay based on an amplitude of a respective one of the one or more frequency envelopes.

7. The method according to claim 3, wherein determining, for each of the determined electrodes, a respective delay from the determined temporal reference point comprises determining the respective delay based on an amplitude of a respective one of the one or more frequency envelopes and a frequency of the respective one of the one or more frequency envelopes.

8. The method according to claim 1, wherein the electrodes of the auditory prosthesis are stimulated using single pulses, a periodic pulse train, a group of non periodic pulses, no pulses, asynchronous, interleaved, or concurrent electrical pulses.

9. The method according to claim 1, wherein the electrodes of the auditory prosthesis have forms of grounding selected from common, multipolar, or monopolar.

10. The method according to claim 1, further comprising:
    determining a wait period length before each successive temporal reference point.

11. The method according to claim 10, further comprising:
    providing a wait period of no electrical stimulation after a stimulation window, prior to any subsequent electrode stimulation window, wherein the duration of the wait period is the determined wait period length.

12. A system including a microphone, a signal processor and an electrode array, wherein the system uses a signal processing method, the signal processing method including the following steps:
    dividing an acoustic signal into frequency envelopes;
    determining which electrodes of the electrode array are to be stimulated;
    determining a temporal reference point for stimulating the determined electrodes;
    determining, for each of the determined electrodes, a respective delay from the determined temporal reference point, wherein the respective delay defines how long to wait after the determined temporal reference point before stimulating the respective electrode;
    determining, for each of the determined electrodes, a respective amplitude based on an amplitude of one of the one or more frequency envelopes; and
    stimulating the electrodes of the electrode by applying stimulus to each electrode with the electrode's determined delay and amplitude.

13. The system of claim 12, wherein the signal processing method further comprises:
    determining a wait period length before each successive temporal reference point.

14. An auditory prosthesis having a signal processor, wherein the auditory prosthesis uses a signal processing method, the signal processing method including the following steps:
    dividing an acoustic signal into frequency envelopes;
    determining which electrodes of the auditory prosthesis are to be stimulated;
    determining a temporal reference point for stimulating the determined electrodes;
    determining, for each of the determined electrodes, a respective delay from the determined temporal reference point, wherein the respective delay defines how long to wait after the determined temporal reference point before stimulating the respective electrode;
    determining, for each of the determined electrodes, a respective amplitude based on an amplitude of one of the one or more frequency envelopes; and stimulating the determined electrodes of the auditory prosthesis by applying stimulus to each electrode with the electrode's determined delay and amplitude.

15. The auditory prosthesis of claim 14, wherein the signal processing method further comprises:
determining a wait period length before each successive temporal reference point.

* * * * *